United States Patent [19]
Creasy et al.

[11] Patent Number: 6,165,766
[45] Date of Patent: Dec. 26, 2000

[54] HUMAN PROTEIN KINASES HYAK3

[75] Inventors: Caretha L. Creasy, Norristown, Pa.; Wei Xie, Hunan, China

[73] Assignee: SmithKline Beecham Corporation, Philadelphia, Pa.

[21] Appl. No.: 09/359,257

[22] Filed: Jul. 22, 1999

Related U.S. Application Data

[62] Division of application No. 08/835,170, Apr. 7, 1997, Pat. No. 5,965,420.
[60] Provisional application No. 60/040,618, Mar. 5, 1997.

[51] Int. Cl.[7] ..................................... C12N 9/12
[52] U.S. Cl. ..................... 435/194; 536/23.2; 536/23.5
[58] Field of Search ........................... 435/194; 536/23.2, 536/23.5

[56] References Cited

FOREIGN PATENT DOCUMENTS

WO 96/27015   6/1996   WIPO .

OTHER PUBLICATIONS

Garrett et al., "Loss of Ras activity in *Saccharomyces cerevisiae* is suppressed by disruptions of etc.". *Genes & Development*, 3:1336–1348 (1989).
Accession No. Z50142, Gentles et al., "Direct Submission" Jul. 1995.
Accession No. Z70308, Wilson et al., "Direct Submission" Mar. 1996.
Accession No. H62028, Hillier et al., Homo sapiens cDNA clone 209224 Similar to yeast protein kinase YAKI, Oct. 1995, EMBL Sequence Database.
Accession No. AA002193, "Homo sapiens cDNA clone 428049 similar to serine/threonine kinase c16c9.7", Jul. 1996, EMBL Sequence Database.
Tugendreich S. et al., "Linking Yeast Genetics t Mammalia Genomes: Identification and Mapping of the Human Homolog of CDC27 Via the Expressed Sequence Tag Database" Proc. Natl. Acad. of Science, vol. 90 (21), Nov. 1993, pp. 10031–10035.
Garrett S. et al., "The *Saccharomyces cerevisiae* yaki gene encodes of protein that is induced by arrest early in the cell cycle", Molecular and Cellular Biology, vol. 11(8), pp. 4045–4052, Aug. 1991.
Accession No. Y12735, Becker et al., "Homo sapiens mRNA for protein kinase Dyrk3", Jan. 1998, EMBL Sequence Database.

*Primary Examiner*—Nashaat T. Nashed
*Attorney, Agent, or Firm*—William T. Han; Ratner & Prestia; William T. King

[57] ABSTRACT hYAK3 polypeptides and polynucleotides and methods for producing such polypeptides by recombinant techniques are disclosed. Also disclosed are methods for utilizing hYAK3 polypeptides and polynucleotides in the design of protocols for the treatment of bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome., among others, and diagnostic assays for such conditions.

4 Claims, 4 Drawing Sheets

Nucleotide and Amino Acid sequence from a hYAK3α (SEQ ID NOS: 1 and 2, respectively.)

```
   1 GGAGCGAAATGCGCTGAGCTGCAGTGTCTGGTCGAGAGTACCCGTGGGAGCGTCGCGCCG    60
  61 CGGAGGCAGCCGTCCCGGCGTAGGTGGCGTGGCCGACCGGACCCCCAACTGGCGCCTCTC   120
 121 CCCGCGCGGGGTCCCGAGCTAGGAGATGGGAGGCACAGCTCGTGGGCCTGGGCGGAAGGA   180
                                  M  G  G  T  A  R  G  P  G  R  K  D
 181 TGCGGGGCCGCCTGGGGCCGGGCTCCCGCCCCAGCAGCGGAGGTTGGGGGATGGTGTCTA   240
      A  G  P  P  G  A  G  L  P  P  Q  Q  R  R  L  G  D  G  V
 241 TGACACCTTCATGATGATAGATGAAACCAAATGTCCCCCCTGTTCAAATGTACTCTGCAA   300
      D  T  F  M  M  I  D  E  T  K  C  P  P  C  S  N  V  L  C  N
 301 TCCTTCTGAACCACCTCCACCCAGAAGACTAAATATGACCACTGAGCAGTTTACAGGAGA   360
      P  S  E  P  P  P  P  R  R  L  N  M  T  T  E  Q  F  T  G  D
 361 TCATACTCAGCACTTTTTGGATGGAGGTGAGATGAAGGTAGAACAGCTGTTTCAAGAATT   420
      H  T  Q  H  F  L  D  G  G  E  M  K  V  E  Q  L  F  Q  E  F
 421 TGGCAACAGAAAATCCAATACTATTCAGTCAGATGGCATCAGTGACTCTGAAAAATGCTC   480
      G  N  R  K  S  N  T  I  Q  S  D  G  I  S  D  S  E  K  C  S
 481 TCCTACTGTTTCTCAGGGTAAAAGTTCAGATTGCTTGAATACAGTAAAATCCAACAGTTC   540
      P  T  V  S  Q  G  K  S  S  D  C  L  N  T  V  K  S  N  S  S
 541 ATCCAAGGCACCCAAAGTGGTGCCTCTGACTCCAGAACAAGCCCTGAAGCAATATAAACA   600
      S  K  A  P  K  V  V  P  L  T  P  E  Q  A  L  K  Q  Y  K  H
 601 CCACCTCACTGCCTATGAGAAACTGGAAATAATTAATTATCCAGAAATTTACTTTGTAGG   660
      H  L  T  A  Y  E  K  L  E  I  I  N  Y  P  E  I  Y  F  V  G
 661 TCCAAATGCCAAGAAAAGACATGGAGTTATTGGTGGTCCCAATAATGGAGGGTATGATGA   720
      P  N  A  K  K  R  H  G  V  I  G  G  P  N  N  G  G  Y  D  D
 721 TGCAGATGGGGCCTATATTCATGTACCTCGAGACCATCTAGCTTATCGATATGAGGTGCT   780
      A  D  G  A  Y  I  H  V  P  R  D  H  L  A  Y  R  Y  E  V  L
 781 GAAAATTATTGGCAAGGGGAGTTTTGGGCAGGTGGCCAGGGTCTATGATCACAAACTTCG   840
      K  I  I  G  K  G  S  F  G  Q  V  A  R  V  Y  D  H  K  L  R
 841 ACAGTACGTGGCCCTAAAAATGGTGCGCAATGAGAAGCGCTTTCATCGTCAAGCAGCTGA   900
      Q  Y  V  A  L  K  M  V  R  N  E  K  R  F  H  R  Q  A  A  E
 901 GGAGATCCGGATTTTGGAGCATCTTAAGAAACAGGATAAAACTGGTAGTATGAACGTTAT   960
      E  I  R  I  L  E  H  L  K  K  Q  D  K  T  G  S  M  N  V  I
 961 CCACATGCTGGAAAGTTTCACATTCCGGAACCATGTTTGCATGGCCTTTGAATTGCTGAG  1020
      H  M  L  E  S  F  T  F  R  N  H  V  C  M  A  F  E  L  L  S
1021 CATAGACCTTTATGAGCTGATTAAAAAAAAATAAGTTTCAGGGTTTTAGCGTCCAGTTGGT  1080
      I  D  L  Y  E  L  I  K  K  N  K  F  Q  G  F  S  V  Q  L  V
1081 ACGCAAGTTTGCCCAGTCCATCTTGCAATCTTTGGATGCCCTCCACAAAAATAAGATTAT  1140
      R  K  F  A  Q  S  I  L  Q  S  L  D  A  L  H  K  N  K  I  I
1141 TCACTGCGATCTGAAGCCAGAAAACATTCTCCTGAAACACCACGGGCGCAGTTCAACCAA  1200
      H  C  D  L  K  P  E  N  I  L  L  K  H  H  G  R  S  S  T  K
1201 GGTCATTGACTTTGGGTCCAGCTGTTTCGAGTACCAGAAGCTCTACACATATATCCAGTC  1260
      V  I  D  F  G  S  S  C  F  E  Y  Q  K  L  Y  T  Y  I  Q  S
1261 TCGGTTCTACAGAGCTCCAGAAATCATCTTAGGAAGCCGCTACAGCACACCAATTGACAT  1320
      R  F  Y  R  A  P  E  I  I  L  G  S  R  Y  S  T  P  I  D  I
1321 ATGGAGTTTTGGCTGCATCCTTGCAGAACTTTTAACAGGACAGCCTCTCTTCCCTGGAGA  1380
      W  S  F  G  C  I  L  A  E  L  L  T  G  Q  P  L  F  P  G  E
1381 GGATGAAGGAGACCAGTTGGCCTCCATGATGGAGCTTCTAGGGATGCCACCACCAAAACT  1440
      D  E  G  D  Q  L  A  S  M  M  E  L  L  G  M  P  P  P  K  L
```

FIG. 1A

```
1441  TCTGGAGCAATCCAAACGTGCCAAGTACTTTATTAATTCCAAGGGCATACCCCGCTACTG  1500
       L   E   Q   S   K   R   A   K   Y   F   I   N   S   K   G   I   P   R   Y   C
1501  CTCTGTGACTACCCAGGCAGATGGGAGGGTTGTGCTTGTGGGGGGTCGCTCACGTAGGGG  1560
       S   V   T   T   Q   A   D   G   R   V   V   L   V   G   G   R   S   R   R   G
1561  TAAAAAGCGGGGTCCCCCAGGCAGCAAAGACTGGGGACAGCACTGAAAGGGTGTGATGA  1620
       K   K   R   G   P   P   G   S   K   D   W   G   T   A   L   K   G   C   D   D
1621  CTACTTGTTTATAGAGTTCTTGAAAAGGTGTCTTCACTGGGACCCCTCTGCCCGCTTGAC  1680
       Y   L   F   I   E   F   L   K   R   C   L   H   W   D   P   S   A   R   L   T
1681  CCCAGCTCAAGCATTAAGACACCCTTGGATTAGCAAGTCTGTCCCCAGACCTCTCACCAC  1740
       P   A   Q   A   L   R   H   P   W   I   S   K   S   V   P   R   P   L   T   T
1741  CATAGACAAGGTGTCAGGGAAACGGGTAGTTAATCCTGCAAGTGCTTTCCAGGGATTGGG  1800
       I   D   K   V   S   G   K   R   V   V   N   P   A   S   F   Q   G   L   G
1801  TTCTAAGCTGCCTCCAGTTGTTGGAATAGCCAATAAGCTTAAAGCTAACTTAATGTCAGA  1860
       S   K   L   P   P   V   V   G   I   A   N   K   L   K   A   N   L   M   S   E
1861  AACCAATGGTAGTATACCCCTATGCAGTGTATTGCCAAAACTGATTAGCTAGTGGACAGA  1920
       T   N   G   S   I   P   L   C   S   V   L   P   K   L   I   S
1921  GATATGCCCAGAGATGCATATGTGTATATTTTTATGATCTTACAAACCTGCAAATGGAAA  1980
1981  AAATGCAAGCCCATTGGTGGATGTTTTTGTTAGAGTAGACTTTTTTTAAACAAGACAAAA  2040
2041  CATTTTTATATGATTATAAAA                                        2061
```

FIG. 1B

Nucleotide and Amino Acid sequence from a hYAK3b (SEQ ID NOS: 3 and 4, respectively.)

```
   1 CGGCGCTGGCAAGCGAAGCTTGGGGGTGGGGAGGTAGAGTGAGCCCTCAGTAGGAGGGAC     60
  61 GAGGGCAGGGGTCTGACTGCCTCCCCGGGACCGCCCCCACCTCCTCTCTATCAGGGCCCC    120
 121 CTCCCCCCATCCCTGTCTCACCGGGCGCGGGGACGGGGCTAGAGCGGAGTTAGAGCAAG    180
 181 AAGAATTTCCACCCCTGGATTCCCTCTGAAACCCTAGATCGGGGTATATGTTAAGGGATT    240
 241 ACGAAAATCTAGGACTTTTTGTGGGGCTTTTTATTAAAGGGGGGGAGCCCGGGAGCAATA    300
 301 CCTTGGAAAGAAGCCCTGTTGCTTAGAGCGGATAACCAACGGCTGAACTCTTGGGGTTTG    360
 361 CTGTGAGGGGTGCGGTCTAGCTTCGAATGTACAGTGGTGGAGCCACAGTGTTAAAGAACA    420
 421 GAGAAGTGATCCTTAATCATTTAGAATTTTGCCTCCACCATCCACCAGAAAATGAAGTGG    480
                                                        M  K  W
 481 AAAGAGAAGTTGGGGGATGGTGTCTATGACACCTTCATGATGATAGATGAAACCAAATGT    540
      K  E  K  L  G  D  G  V  Y  D  T  F  M  M  I  D  E  T  K  C
 541 CCCCCCTGTTCAAATGTACTCTGCAATCCTTCTGAACCACCTCCACCCAGAAGACTAAAT    600
      P  P  C  S  N  V  L  C  N  P  S  E  P  P  P  P  R  R  L  N
 601 ATGACCACTGAGCAGTTTACAGGAGATCATACTCAGCACTTTTTGGATGGAGGTGAGATG    660
      M  T  T  E  Q  F  T  G  D  H  T  Q  H  F  L  D  G  G  E  M
 661 AAGGTAGAACAGCTGTTTCAAGAATTTGGCAACAGAAAATCCAATACTATTCAGTCAGAT    720
      K  V  E  Q  L  F  Q  E  F  G  N  R  K  S  N  T  I  Q  S  D
 721 GGCATCAGTGACTCTGAAAAATGCTCTCCTACTGTTTCTCAGGGTAAAAGTTCAGATTGC    780
      G  I  S  D  S  E  K  C  S  P  T  V  S  Q  G  K  S  S  D  C
 781 TTGAATACAGTAAAATCCAACAGTTCATCCAAGGCACCCAAAGTGGTGCCTCTGACTCCA    840
      L  N  T  V  K  S  N  S  S  S  K  A  P  K  V  V  P  L  T  P
 841 GAACAAGCCCTGAAGCAATATAAACACCACCTCACTGCCTATGAGAAACTGGAAATAATT    900
      E  Q  A  L  K  Q  Y  K  H  H  L  T  A  Y  E  K  L  E  I  I
 901 AATTATCCAGAAATTTACTTTGTAGGTCCAAATGCCAAGAAAAGACATGGAGTTATTGGT    960
      N  Y  P  E  I  Y  F  V  G  P  N  A  K  K  R  H  G  V  I  G
 961 GGTCCCAATAATGGAGGGTATGATGATGCAGATGGGGCCTATATTCATGTACCTCGAGAC   1020
      G  P  N  N  G  G  Y  D  D  A  D  G  A  Y  I  H  V  P  R  D
1021 CATCTAGCTTATCGATATGAGGTGCTGAAAATTATTGGCAAGGGGAGTTTTGGGCAGGTG   1080
      H  L  A  Y  R  Y  E  V  L  K  I  I  G  K  G  S  F  G  Q  V
1081 GCCAGGGTCTATGATCACAAACTTCGACAGTACGTGGCCCTAAAAATGGTGCGCAATGAG   1140
      A  R  V  Y  D  H  K  L  R  Q  Y  V  A  L  K  M  V  R  N  E
1141 AAGCGCTTTCATCGTCAAGCAGCTGAGGAGATCCGGATTTTGGAGCATCTTAAGAAACAG   1200
      K  R  F  H  R  Q  A  A  E  E  I  R  I  L  E  H  L  K  K  Q
1201 GATAAAACTGGTAGTATGAACGTTATCCACATGCTGGAAAGTTTCACATTCCGGAACCAT   1260
      D  K  T  G  S  M  N  V  I  H  M  L  E  S  F  T  F  R  N  H
1261 GTTTGCATGGCCTTTGAATTGCTGAGCATAGACCTTTATGAGCTGATTAAAAAAAATAAG   1320
      V  C  M  A  F  E  L  L  S  I  D  L  Y  E  L  I  K  K  N  K
1321 TTTCAGGGTTTTAGCGTCCAGTTGGTACGCAAGTTTGCCCAGTCCATCTTGCAATCTTTG   1380
      F  Q  G  F  S  V  Q  L  V  R  K  F  A  Q  S  I  L  Q  S  L
1381 GATGCCCTCCACAAAAATAAGATTATTCACTGCGATCTGAAGCCAGAAAACATTCTCCTG   1440
      D  A  L  H  K  N  K  I  I  H  C  D  L  K  P  E  N  I  L  L
1441 AAACACCACGGGCGCAGTTCAACCAAGGTCATTGACTTTGGGTCCAGCTGTTTCGAGTAC   1500
      K  H  H  G  R  S  S  T  K  V  I  D  F  G  S  S  C  F  E  Y
```

FIG. 2A

```
1501  CAGAAGCTCTACACATATATCCAGTCTCGGTTCTACAGAGCTCCAGAAATCATCTTAGGA  1560
       Q   K   L   Y   T   Y   I   Q   S   R   F   Y   R   A   P   E   I   I   L   G
1561  AGCCGCTACAGCACACCAATTGACATATGGAGTTTTGGCTGCATCCTTGCAGAACTTTTA  1620
       S   R   Y   S   T   P   I   D   I   W   S   F   G   C   I   L   A   E   L   L
1621  ACAGGACAGCCTCTCTTCCCTGGAGAGGATGAAGGAGACCAGTTGGCCTCCATGATGGAG  1680
       T   G   Q   P   L   F   P   G   E   D   E   G   D   Q   L   A   S   M   M   E
1681  CTTCTAGGGATGCCACCACCAAAACTTCTGGAGCAATCCAAACGTGCCAAGTACTTTATT  1740
       L   L   G   M   P   P   P   K   L   L   E   Q   S   K   R   A   K   Y   F   I
1741  AATTCCAAGGGCATACCCCGCTACTGCTCTGTGACTACCCAGGCAGATGGGAGGGTTGTG  1800
       N   S   K   G   I   P   R   Y   C   S   V   T   T   Q   A   D   G   R   V   V
1801  CTTGTGGGGGGTCGCTCACGTAGGGGTAAAAAGCGGGGTCCCCCAGGCAGCAAAGACTGG  1860
       L   V   G   G   R   S   R   R   G   K   K   R   G   P   P   G   S   K   D   W
1861  GGGACAGCACTGAAAGGGTGTGATGACTACTTGTTTATAGAGTTCTTGAAAAGGTGTCTT  1920
       G   T   A   L   K   G   C   D   D   Y   L   F   I   E   F   L   K   R   C   L
1921  CACTGGGACCCCTCTGCCCGCTTGACCCCAGCTCAAGCATTAAGACACCCTTGGATTAGC  1980
       H   W   D   P   S   A   R   L   T   P   A   Q   A   L   R   H   P   W   I   S
1981  AAGTCTGTCCCCAGACCTCTCACCACCATAGACAAGGTGTCAGGGAAACGGGTAGTTAAT  2040
       K   S   V   P   R   P   L   T   T   I   D   K   V   S   G   K   R   V   V   N
2041  CCTGCAAGTGCTTTCCAGGGATTGGGTTCTAAGCTGCCTCCAGTTGTTGGAATAGCCAAT  2100
       P   A   S   A   F   Q   G   L   G   S   K   L   P   P   V   V   G   I   A   N
2101  AAGCTTAAAGCTAACTTAATGTCAGAAACCAATGGTAGTATACCCCTATGCAGTGTATTG  2160
       K   L   K   A   N   L   M   S   E   T   N   G   S   I   P   L   C   S   V   L
2161  CCAAAACTGATTAGCTAGTGGACAGAGATATGCCCAGAGATGCATATGTGTATATTTTA   2220
       P   K   L   I   S
2221  TGATCTTACAAACCTGCAAATGGAAAAAATGCAAGCCCATTGGTGGATGTTTTGTTAGA  2280
2281  GTAGACTTTTTTAAACAAGACAAAACATTTTTATATGATTATAAAA               2327
```

FIG. 2B

HUMAN PROTEIN KINASES HYAK3

This is a divisional of application Ser. No. 08/835,170 filed Apr. 7, 1997, now U.S. Pat. No. 5,965,420 which claims priority of provisional application 60/040,618 filed Mar 5, 1997. Both applications are incorporated by reference in their entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to a serine/threonine protein kinase, hereinafter referred to as hYAK3. The invention also relates to inhibiting or activating the action of such polynucleotides and polypeptides.

BACKGROUND OF THE INVENTION

A number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein serine/threonine kinases (PSTK) and phosphatases. Serine/threonine phosphorylation is a major mediator of signal transduction in multicellular organisms. Receptor-bound, membrane-bound and intracellular PSTKs regulate cell proliferation, cell differentiation and signalling processes in many cell types.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are potential targets for drug design.

A subset of PSTKs are involved in regulation of cell cycling. These are the cyclin-dependent kinases or CDKs (Peter and Herskowitz, Cell 1994: 79, 181–184). CDKs are activated by binding to regulatory proteins called cyclins and control passage of the cell through specific cell cycle checkpoints. For example, CDK2 complexed with cyclin E allows cells to progress through the G1 to S phase transition. The complexes of CDKs and cyclins are subject to inhibition by low molecular weight proteins such as p16 (Serrano et al, Nature 1993: 366, 704), which binds to and inhibits CDK4. Deletions or mutations in p16 have been implicated in a variety of tumors (Kamb et al, Science 1994: 264, 436–440). Therefore, the proliferative state of cells and diseases associated with this state are dependent on the activity of CDKs and their associated regulatory molecules. In diseases such as cancer where inhibition of proliferation is desired, compounds that inhibit CDKs may be useful therapeutic agents. Conversely, activators of CDKs may be useful where enhancement of proliferation is needed, such as in the treatment of immunodeficiency.

YAK1, a PSTK with sequence homology to CDKs, was originally identified in yeast as a mediator of cell cycle arrest caused by inactivation of the cAMP-dependent protein kinase PKA (Garrett et al, Mol Cell Biol. 1991: 11, 4045–4052). YAK1 kinase activity is low in cycling yeast but increases dramatically when the cells are arrested prior to the S-G2 transition. Increased expression of YAK1 causes growth arrest in yeast cells deficient in PKA. Therefore, YAK1 can act as a cell cycle suppressor in yeast.

Frequently, in disease such as osteoporosis and osteoarthritis, patients have established lesions of bone or cartilage, respectively. Treatment of such lesions requires an agent that will stimulate new bone or cartilage formation to replace that lost to the disease; therefore, there is a need for drugs that increase the number of osteoblasts or chondrocytes, the cells responsible for bone or cartilage formation, respectively. Similarly, replacement of heart or skeletal muscle depleted by diseases such as myocardial infarction or HIV-associated cachexia requires drugs that stimulate proliferation of cardiac myocytes or skeletal myoblasts. The present invention describes a novel human homolog of yeast YAK1 termed hYAK3, which is expressed predominantly in testis and skeletal muscle. The sequence of hYAK3 shares homology with predicted PSTKs from C. elegans, S. pombe and S. cerevisiae and has motifs associated with known protein kinases. Inhibitors of hYAK3 are expected to stimulate proliferation of cells in which it is expressed.

This indicates that these serine/threonine protein kinases have an established, proven history as therapeutic targets. Clearly there is a need for identification and characterization of further members of the serine/threonine protein kinase family which can play a role in preventing, ameliorating or correcting dysfunctions or diseases, including, but not limited to, bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to hYAK3 polypeptides and recombinant materials and methods for their production. Another aspect of the invention relates to methods for using such hYAK3 polypeptides and polynucleotides. Such uses include the treatment of bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome., among others. In still another aspect, the invention relates to methods to identify agonists and antagonists using the materials provided by the invention, and treating conditions associated with hYAK3 imbalance with the identified compounds. Yet another aspect of the invention relates to diagnostic assays for detecting diseases associated with inappropriate hYAK3 activity or levels.

BRIEF DESCRIPTION OF THE DRAWINGS

FIG. 1 shows the nucleotide and deduced amino acid sequence from human hYAK3α. SEQ ID NOS: 1 and 2.

FIG. 2 shows the nucleotide and deduced amino acid sequence from human hYAK3β. SEQ ID NOS: 3 and 4.

DESCRIPTION OF THE INVENTION

Definitions

The following definitions are provided to facilitate understanding of certain terms used frequently herein.

"hYAK3" refers, among others, generally to a polypeptide having the amino acid sequence set forth in SEQ ID NO:2 or 4 or an allelic variant thereof.

"hYAK3 activity or hYAK3 polypeptide activity" or "biological activity of the hYAK3 or hYAK3 polypeptide" refers to the metabolic or physiologic function of said hYAK3 including similar activities or improved activities or these activities with decreased undesirable side-effects. Also included are antigenic and immunogenic activities of said hYAK3.

"hYAK3 gene" refers to a polynucleotide having the nucleotide sequence set forth in SEQ ID NO: 1 or 3 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides. "Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS - STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, N.J., 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, N.Y., 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S.F. et al., *J Molec Biol* (1990) 215:403).

Polypeptides of the Invention

In one aspect, the present invention relates to hYAK3 polypeptides. The hYAK3 polypeptides include the polypeptide of SEQ ID NO:2 or 4; as well as polypeptides comprising the amino acid sequence of SEQ ID NO: 2 or 4; and polypeptides comprising the amino acid sequence which have at least 80% identity to that of SEQ ID NO:2 or 4 over its entire length, and still more preferably at least 90% identity, and even still more preferably at least 95% identity to SEQ ID NO: 2 or 4. Also included within hYAK3 polypeptides are polypeptides having the amino acid sequence which have at least 80% identity to the polypeptide having the amino acid sequence of SEQ ID NO:2 or 4 over its entire length, and still more preferably at least 90% identity, and still more preferably at least 95% identity to SEQ ID NO:2 or 4. Preferably hYAK3 polypeptide exhibit at least one biological activity of hYAK3.

The hYAK3 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the hYAK3 polypeptides are also included in the invention. A fragment is a polypeptide having an amino acid sequence that entirely is the same as part, but not all, of the amino acid sequence of the aforementioned hYAK3 polypeptides. As with hYAK3 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of hYAK3 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of hYAK3 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate hYAK3 activity, including those with a similar activity or an improved activity, or with a decreased undesirable activity. Also included are those that are antigenic or immunogenic in an animal, especially in a human.

Preferably, all of these polypeptide fragments retain the biological activity of the hYAK3, including antigenic activity. Variants of the defined sequence and fragments also form part of the present invention. Preferred variants are those that vary from the referents by conservative amino acid substitutions–i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The hYAK3 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to hYAK3 polynucleotides. hYAK3 polynucleotides include isolated polynucleotides which encode the hYAK3 polypeptides and fragments, and polynucleotides closely related thereto. More specifically, hYAK3 polynucleotide of the invention include a polynucleotide comprising the nucleotide sequence set forth in SEQ ID NO:1 or 3 encoding a hYAK3 polypeptide of SEQ ID NO: 2 or 4, and polynucleotide having the particular sequence of SEQ ID NO:1 or 3. hYAK3 polynucleotides further include a polynucleotide comprising a nucleotide sequence that has at least 80% identity to a nucleotide sequence encoding the hYAK3 polypeptide of SEQ ID NO:2 or 4 over its entire length, and a polynucleotide that is at least 80% identical to that having SEQ ID NO: 1 or 3 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under hYAK3 polynucleotides are a nucleotide sequence which has sufficient identity to a nucleotide sequence contained in SEQ ID NO: 1 or 3 to hybridize under conditions useable for amplification or for use as a probe or marker. The invention also provides polynucleotides which are complementary to such hYAK3 polynucleotides.

hYAK3 of the invention is structurally related to other proteins of the serine/threonine protein kinase family, as shown by the results of sequencing the cDNA encoding human hYAK3. The cDNA sequence contains an open reading frame encoding a polypeptide of 588/568 (α and β forms, respectively) amino acids. Amino acid of sequence of FIGS. 1 and 2 (SEQ ID NOS:2 and 4, respectively) has about 65% identity (using FASTA) in 402 amino acid residues with *C elegans* protein kinase F49E 11.1. Furthermore, hYAK3 is 49% identical to *S. pombe* protein kinase SPAC2F7.03c over 315 amino acids (Barrell et al., *Schizosaccahromyces pombe* chromosome I sequencing project, 1995) and 46% identical to *S. cerevisiae* protein kinase YAK1 over 286 amino acids (Garrett and Broach, Genes & Develop. 3:1336–1348, 1989). Nucleotide sequence of FIGS. 1 and 2 (SEQ ID NOS :1 and 4, respectively) has about 64% identity (using FASTA) in 672 nucleotide residues with *C. elegans* protein kinase F49E11.1.

One polynucleotide of the present invention encoding hYAK3 may be obtained using standard cloning and screening, from a cDNA library derived from mnRNA in cells of human testis and skeletal muscle using the expressed sequence tag (EST) analysis (Adams, M.D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding hYAK3 polypeptide of SEQ ID NO:2 or 4 may be identical over its entire length to the coding sequence set forth in FIG. 1 or 2 (SEQ ID NO: 1 or 3), or may be a degenerate form of this nucleotide sequence encoding the polypeptide of SEQ ID NO:2 or 4, or may be highly identical to a nucleotide sequence that encodes the polypeptide of SEQ ID NO:2 or 4. Preferably, the polynucleotides of the invention comprise a nucleotide sequence that is highly identical, at least 80% identical, with a nucleotide sequence encoding a hYAK3 polypeptide, or at least 80% identical with the sequence contained in FIG. 1 or 2 (SEQ ID NO: 1 or 3) encoding hYAK3 polypeptide, or at least 80% identical to a nucleotide sequence encoding the polypeptide of SEQ ID NO:2 or 4.

When the polynucleotides of the invention are used for the recombinant production of hYAK3 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding hYAK3 variants comprise the amino acid sequence hYAK3 polypeptide of FIG. 1 or 2 (SEQ ID NO:2 or 4) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO:1 or 3, may be used as hybridization probes for cDNA and genomic DNA, to isolate full-length cDNAs and genomic clones encoding hYAK3 polypeptide and to isolate cDNA and genomic clones of other genes that have a high sequence similarity to the hYAK3 gene. Such hybridization techniques are known to those of skill in the art. Typically these nucleotide sequences are 70% identical preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding hYAK3 comprises the steps of screening an appropriate library under stringent hybridization conditions with a labeled probe having the SEQ ID NO: 1 or 3 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 nM sodium phosphate (pH7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the hYAK3 polypeptide is to be expressed for use in screening assays, generally, it is preferred that the polypeptide be produced at the surface of the cell. In this event, the cells may be harvested prior to use in the screening assay. If hYAK3 polypeptide is secreted into the medium, the medium can be recovered in order to recover and purify the polypeptide; if produced intracellularly, the cells must first be lysed before the polypeptide is recovered. hYAK3 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of hYAK3 polynucleotides for use as diagnostic reagents. Detection of a mutated form of hYAK3 gene associated with a dysfunction will provide a diagnostic tool that can add to or define a diagnosis of a disease or susceptibility to a disease which results from under-expression, over-expression or altered expression of hYAK3. Individuals carrying mutations in the hYAK3 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled hYAK3 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al, Science (1985) 230:1242. Sequence changes at specific locations may also be revealed by nuclease protection assays, such as RNase and S1 protection or the chemical cleavage method. See Cotton et al, Proc Natl Acad Sci USA (1985) 85:4397–4401. In another embodiment, an array of oligonucleotides probes comprising hYAK3 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. through detection of mutation in the hYAK3 gene by the methods described.

In addition, bone loss including osteoporosis; inflammatory diseases such as Adult Respiratory Disease Syndrome (ARDS), Rheumatoid arthritis, Osteoarthritis, lnflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension;

hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome., can be diagnosed by methods comprising determining from a sample derived from a subject an abnormally decreased or increased level of hYAK3 polypeptide or hYAK3 mRNA. Decreased or increased expression can be measured at the RNA level using any of the methods well known in the art for the quantization of polynucleotides, such as, for example, PCR, RT-PCR, RNase protection, Northern blotting and other hybridization methods. Assay techniques that can be used to determine levels of a protein, such as an hYAK3 polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the hYAK3 polypeptides. The term "immunospecific" means that the antibodies have substantial greater affinity for the polypeptides of the invention than their affinity for other related polypeptides in the prior art.

Antibodies generated against the hYAK3 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al, *Immunology Today* (1983) 4:72) and the EBV-hybridora technique (Cole et al, MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against hYAK3 polypeptides may also be employed to treat bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome., among others.

Vaccines

Another aspect of the invention relates to a method for inducing an immunological response in a mammal which comprises inoculating the mammal with hYAK3 polypeptide, or a fragment thereof, adequate to produce antibody and/or T cell immune response to protect said animal from bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome., among others. Yet another aspect of the invention relates to a method of inducing immunological response in a mammal which comprises, delivering hYAK3 polypeptide via a vector directing expression of hYAK3 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a hYAK3 polypeptide wherein the composition comprises a hYAK3 polypeptide or hYAK3 gene. The vaccine formulation may further comprise a suitable carrier. Since hYAK3 polypeptide may be broken down in the stomach, it is preferably administered parenterally (including subcutaneous, intramuscular, intravenous, intradermal etc. injection). Formulations suitable for parenteral administration include aqueous and nonaqueous sterile injection solutions which may contain antioxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The hYAK3 polypeptide of the present invention may be employed in a screening process for compounds which activate (agonists) or inhibit activation of (antagonists, or otherwise called inhibitors) the hYAK3 polypeptide of the present invention. Thus, polypeptides of the invention may also be used to assess identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al, *Current Protocols in Immunology* 1(2):Chapter 5 (1991).

hYAK3 polypeptides are ubiquitous in the mammalian host and are responsible for many biological functions, including many pathologies. Accordingly, it is desirous to find compounds and drugs which stimulate hYAK3 polypeptide on the one hand and which can inhibit the function of hYAK3 polypeptide on the other hand. In general, agonists are employed for therapeutic and prophylactic purposes for such conditions as bone loss including osteoporosis; inflammatory diseases such as Adult Respiratory Disease Syndrome (ARDS), Rheumatoid arthritis, Osteoarthritis, Inflammatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists ray be employed for a variety of therapeutic and prophylactic purposes for such conditions as bone loss including osteoporosis; inflammatory diseases such as Adult Respiratory Disease Syndrome (ARDS), Rheumatoid arthritis, Osteoarthritis, Inflamrnmatory Bowel Disease (IBD), psoriasis, dermatitis, asthma, allergies; infections such as bacterial, fungal, protozoan and viral infections, particularly infections caused by HIV-1 or HIV-2; HIV-associated cachexia and other immunodeficiency disorders; septic shock; pain; injury; cancers including testicular cancer; anorexia; bulimia; Parkinson's disease; cardiovascular disease including restenosis, atherosclerosis, acute heart failure, myocardial infarction; hypotension; hypertension; urinary retention; angina pectoris; ulcers; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures may involve using appropriate cells which express the hYAK3 polypeptide or respond to hYAK3 polypeptide of the present invention. Such cells include cells from mammals, yeast, *Drosophila* or *E. coli*. Cells which express the hYAK3 polypeptide (or cell membrane containing the expressed polypeptide) or respond to hYAK3 polypeptide are then contacted with a test compound to observe binding, or stimulation or inhibition of a functional response. The ability of the cells which were contacted with the candidate compounds is compared with the same cells which were not contacted for hYAK3 activity.

The knowledge that the hYAK3 encodes a protein kinase suggests that recombinant forms can be used to establish a protein kinase activity. Typically this would involve the direct incubation of hYAK3 with a protein or peptide substrate in the presence of γ-32P- ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While the specific substrates are not yet known, candidates include hYAK3 itself (autophosphorylation), myelin basic protein, casein, histone and HSP27. Other substances might be discovered by incubating hYAK3 with random peptides conjugated to solid supports or displayed on the surface of phage or by incubation of hYAK3 with mammalian cell lysates and γ-32P- ATP, followed by separation of the labelled target proteins, and sequencing. The protein kinase activity of hYAK3 may require incubation with a specific upstream effector. This may be achieved by preincubating HYAK3 with lysates from a variety of stimulated eukaryotic cells and ATP. These assays permit the discovery and modification of compounds which inhibit hYAK3 kinase activity in vitro and would be expected to have effects on proliferation of osteoblasts, chondorcytes, cardiac myocytes or skeletal myoblasts. Any inhibitors so identified would be expected to have up-regulatory effects on proliferation and be useful as a therapeutic for the treatment and prevention of diseases such as osteoporosis, osteoarthritis, cardiomyopathy and chachexia.

This invention contemplates the treatment and/or amelioration of such diseases by administering an hYAK3 inhibiting amount of a compound. Without wishing to be bound by any particular theory of the functioning of the hYAK3 of this invention, it is believed that among the useful inhibitors of hYAK3 function are those compounds which inhibit the kinase activity of the hYAK3. Other sites of inhibition are, of course, possible owing to its position in a signal transduction cascade. Therefore, inhibiting the interaction of hYAK3 with one or more of its upstream or downstream modulators/substrates is also contemplated by this invention. Inhibitors of protein-protein interactions between hYAK3 and other factors could lead to the development of pharmaceutical agents for the modulation of hYAK3 activity.

The assays may simply test binding of a candidate compound wherein adherence to the cells bearing the hYAK3 polypeptide is detected by means of a label directly or indirectly associated with the candidate compound or in an assay involving competition with a labeled competitor.

Further, these assays may test whether the candidate compound results in a signal generated by activation of the hYAK3 polypeptide, using detection systems appropriate to the cells bearing the hYAK3 polypeptide. Inhibitors of activation are generally assayed in the presence of a known agonist and the effect on activation by the agonist by the presence of the candidate compound is observed. Standard methods for conducting such screening assays are well understood in the art.

Examples of potential hYAK3 polypeptide antagonists include antibodies or, in some cases, oligonucleotides or proteins which are closely related to the ligands, substrates, receptors, etc., as the case may be, of the hYAK3 polypeptide, e.g., a fragment of the ligands, substrates, receptors, or small molecules which bind to the polypeptide of the present invention but do not elicit a response, so that the activity of the polypeptide is prevented.

Prophylactic and Therapeutic Methods

This invention provides methods of treating an abnormal conditions related to both an excess of and insufficient amounts of hYAK3 polypeptide activity.

If the activity of hYAK3 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the hYAK3 polypeptide, or by inhibiting a second signal, and thereby alleviating the abnormal condition.

In another approach, soluble forms of hYAK3 polypeptides still capable of binding the ligand in competition with endogenous hYAK3 polypeptide may be administered. Typical embodiments of such competitors comprise fragments of the hYAK3 polypeptide.

In still another approach, expression of the gene encoding endogenous hYAK3 polypeptide can be inhibited using expression blocking techniques. Known such techniques involve the use of antisense sequences, either internally generated or separately administered. See, for example, O'Connor, J Neurochem (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of hYAK3 and its activity, several approaches are also available. One approach comprises administering to a subject a therapeutically effective amount of a compound which activates hYAK3 polypeptide, i.e., an agonist as described above, in combination with a pharmaceutically acceptable carrier, to thereby alleviate the abnormal condition. Alternatively, gene therapy may be employed to effect the endogenous production of hYAK3 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of hYAK3 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

EXAMPLE 1

A partial clone was initially identified through random searches of the Human Genome Sciences database. This partial clone (~1 kb) showed significant homology to YAK1 from *S. cerevisiae*. To obtain the full length cDNA: Using the insert of the above partial clone as a probe, 1 M plaques were screened from both a human testis and skeletal muscle cDNA library (Strata gene, LaJolla Calif.). Library screening procedure is described by (Elgin, et al. Stratagies 4: 8–9, 1991). The probes were α-32P labeled, using a Random Primed Labeling Kit (Boheringer Manheir, Germany, Cat. # 1585584 ) and purified by running over Sephadex G-50 columns (Pharmacia Biotech. Cat. # 17-0855-02). The hybirdization and washing conditions were according to J. Sambrook, E. F. Fritch and T. Maniatis (1989) A Laboratory Manaul Second. Ed. Vol. 1 pp. 2.69–2.81 Cold Spring Harbor Laboratory Press, Cold Spring Harbor, N.Y.). Several positive clones were isolated from each library by plaque purification and fragments containing the inserts were excised and sequenced. The longest insert obtained from the skeletal muscle and testis libraries was 2.1 kb and 2.3 kb, respectively (SEQ ID NOS:1 and 3, respectively). The presence of an in-frame stop codon immediately 5' of an initiation codon indicated that both cDNA's were full length. Comparison of these two cDNAs indicates that the 3' most 1844 nucleotides are identical. The skeletal muscle cDNA (hYAK3α) is 266 nucleotides shorter than the testis cDNA (hYAK3β); however, the skeletal muscle cDNA is 20 amino acids longer at the amino terminus than that obtained from the testis library. The presence of the splice site consensus sequence, AGG, suggests that the differences between these two cDNAs may be due to alternative splicing. Fasta analysis show both peptides to have high homology to a putative serine/threonine kinase of unknown function from *C. elegans* (F49E11.1).

EXAMPLE 2

Northern analysis was carried out to determine the distribution of hYAK3 mRNA in human tissues. The original partial clone was radiolabelled with [32P]-dATP using a randomly primed labelling kit. Membranes containing mRNA from multiple human tissues (Clontech #7760-1 and #7759-1)) were hybridized with the probe and washed under high stringency conditions as directed. Hybridized mRNA was visualized by exposing the membranes to X-ray film One major transcript at ~2.3 kb was present in testis. The transcript was not visible in any other tissues; however, dot blot analysis using a Human Master blot (Clontech #7770-1) indicated that hYAK3 is expressed in other tissues including skeletal muscle.

What is claimed is:

1. An isolated polypeptide comprising the amino acid sequence of SEQ ID NO:2.

2. The isolated polypeptide of claim 1 that consists of the amino acid sequence of SEQ ID NO:2.

3. An isolated polypeptide comprising the amino acid sequence of SEQ ID NO:4.

4. The isolated polypeptide of claim 3 that consists of the amino acid sequence of SEQ ID NO:4.

* * * * *

SEQUENCE LISTING

<160> NUMBER OF SEQ ID NOS: 4

<210> SEQ ID NO 1
<211> LENGTH: 2061
<212> TYPE: DNA
<213> ORGANISM: Human

<400> SEQUENCE: 1

```
ggagcgaaat gcgctgagct gcagtgtctg gtcgagagta cccgtgggag cgtcgcgccg      60
cggaggcagc cgtcccggcg taggtggcgt ggccgaccgg acccccaact ggcgcctctc     120
cccgcgcggg gtcccgagct aggagatggg aggcacagct cgtgggcctg ggcggaagga     180
tgcggggccg cctggggccg ggctcccgcc ccagcagcgg aggttggggg atggtgtcta     240
tgacaccttc atgatgatag atgaaaccaa atgtcccccc tgttcaaatg tactctgcaa     300
tccttctgaa ccacctccac ccagaagact aaatatgacc actgagcagt ttacaggaga     360
tcatactcag cacttttttgg atggaggtga gatgaaggta gaacagctgt ttcaagaatt     420
tggcaacaga aaatccaata ctattcagtc agatggcatc agtgactctg aaaaatgctc     480
tcctactgtt tctcagggta aaagttcaga ttgcttgaat acagtaaaat ccaacagttc     540
atccaaggca cccaaagtgg tgcctctgac tccagaacaa gccctgaagc aatataaaca     600
ccacctcact gcctatgaga aactggaaat aattaattat ccagaaattt actttgtagg     660
tccaaatgcc aagaaaagac atggagttat tggtggtccc aataatggag ggtatgatga     720
tgcagatggg gcctatattc atgtacctcg agaccatcta gcttatcgat atgaggtgct     780
gaaaattatt ggcaagggga gttttgggca ggtggccagg gtctatgatc acaaacttcg     840
acagtacgtg gccctaaaaa tggtgcgcaa tgagaagcgc tttcatcgtc aagcagctga     900
ggagatccgg attttggagc atcttaagaa acaggataaa actggtagta tgaacgttat     960
ccacatgctg gaaagtttca cattccggaa ccatgtttgc atggcctttg aattgctgag    1020
catagacctt tatgagctga ttaaaaaaaa taagtttcag ggttttagcg tccagttggt    1080
```

-continued

```
acgcaagttt gcccagtcca tcttgcaatc tttggatgcc ctccacaaaa ataagattat   1140
tcactgcgat ctgaagccag aaaacattct cctgaaacac cacgggcgca gttcaaccaa   1200
ggtcattgac tttgggtcca gctgtttcga gtaccagaag ctctacacat atatccagtc   1260
tcggttctac agagctccag aaatcatctt aggaagccgc tacagcacac caattgacat   1320
atggagtttt ggctgcatcc ttgcagaact tttaacagga cagcctctct tccctggaga   1380
ggatgaagga gaccagttgg cctccatgat ggagcttcta gggatgccac caccaaaact   1440
tctggagcaa tccaaacgtg ccaagtactt tattaattcc aagggcatac cccgctactg   1500
ctctgtgact acccaggcag atgggagggt tgtgcttgtg gggggtcgct cacgtagggg   1560
taaaaagcgg ggtcccccag gcagcaaaga ctgggggaca gcactgaaag ggtgtgatga   1620
ctacttgttt atagagttct tgaaaaggtg tcttcactgg gacccctctg cccgcttgac   1680
cccagctcaa gcattaagac acccttggat tagcaagtct gtccccagac ctctcaccac   1740
catagacaag gtgtcaggga acgggtagt  taatcctgca agtgctttcc agggattggg   1800
ttctaagctg cctccagttg ttggaatagc caataagctt aaagctaact taatgtcaga   1860
aaccaatggt agtataccc  tatgcagtgt attgccaaaa ctgattagct agtggacaga   1920
gatatgccca gagatgcata tgtgtatatt tttatgatct tacaaacctg caaatggaaa   1980
aaatgcaagc ccattggtgg atgttttgt  tagagtagac tttttttaaa caagacaaaa   2040
catttttata tgattataaa a                                             2061
```

<210> SEQ ID NO 2
<211> LENGTH: 588
<212> TYPE: PRT
<213> ORGANISM: Human

<400> SEQUENCE: 2

```
Met Gly Gly Thr Ala Arg Gly Pro Gly Arg Lys Asp Ala Gly Pro Pro
 1               5                  10                  15

Gly Ala Gly Leu Pro Pro Gln Gln Arg Arg Leu Gly Asp Gly Val Tyr
            20                  25                  30

Asp Thr Phe Met Met Ile Asp Glu Thr Lys Cys Pro Pro Cys Ser Asn
        35                  40                  45

Val Leu Cys Asn Pro Ser Glu Pro Pro Pro Arg Arg Leu Asn Met
    50                  55                  60

Thr Thr Glu Gln Phe Thr Gly Asp His Thr Gln His Phe Leu Asp Gly
65                  70                  75                  80

Gly Glu Met Lys Val Glu Gln Leu Phe Gln Glu Phe Gly Asn Arg Lys
                85                  90                  95

Ser Asn Thr Ile Gln Ser Asp Gly Ile Ser Asp Ser Glu Lys Cys Ser
            100                 105                 110

Pro Thr Val Ser Gln Gly Lys Ser Ser Asp Cys Leu Asn Thr Val Lys
        115                 120                 125

Ser Asn Ser Ser Ser Lys Ala Pro Lys Val Val Pro Leu Thr Pro Glu
    130                 135                 140

Gln Ala Leu Lys Gln Tyr Lys His His Leu Thr Ala Tyr Glu Lys Leu
145                 150                 155                 160

Glu Ile Ile Asn Tyr Pro Glu Ile Tyr Phe Val Gly Pro Asn Ala Lys
                165                 170                 175

Lys Arg His Gly Val Ile Gly Gly Pro Asn Asn Gly Gly Tyr Asp Asp
            180                 185                 190

Ala Asp Gly Ala Tyr Ile His Val Pro Arg Asp His Leu Ala Tyr Arg
```

```
                    195                 200                 205
        Tyr Glu Val Leu Lys Ile Ile Gly Lys Gly Ser Phe Gly Gln Val Ala
                    210                 215                 220
        Arg Val Tyr Asp His Lys Leu Arg Gln Tyr Val Ala Leu Lys Met Val
        225                 230                 235                 240
        Arg Asn Glu Lys Arg Phe His Arg Gln Ala Ala Glu Glu Ile Arg Ile
                        245                 250                 255
        Leu Glu His Leu Lys Lys Gln Asp Lys Thr Gly Ser Met Asn Val Ile
                        260                 265                 270
        His Met Leu Glu Ser Phe Thr Phe Arg Asn His Val Cys Met Ala Phe
                    275                 280                 285
        Glu Leu Leu Ser Ile Asp Leu Tyr Glu Leu Ile Lys Lys Asn Lys Phe
                    290                 295                 300
        Gln Gly Phe Ser Val Gln Leu Val Arg Lys Phe Ala Gln Ser Ile Leu
        305                 310                 315                 320
        Gln Ser Leu Asp Ala Leu His Lys Asn Lys Ile Ile His Cys Asp Leu
                        325                 330                 335
        Lys Pro Glu Asn Ile Leu Leu Lys His His Gly Arg Ser Ser Thr Lys
                        340                 345                 350
        Val Ile Asp Phe Gly Ser Ser Cys Phe Glu Tyr Gln Lys Leu Tyr Thr
                    355                 360                 365
        Tyr Ile Gln Ser Arg Phe Tyr Arg Ala Pro Glu Ile Ile Leu Gly Ser
                    370                 375                 380
        Arg Tyr Ser Thr Pro Ile Asp Ile Trp Ser Phe Gly Cys Ile Leu Ala
        385                 390                 395                 400
        Glu Leu Leu Thr Gly Gln Pro Leu Phe Pro Gly Glu Asp Glu Gly Asp
                        405                 410                 415
        Gln Leu Ala Ser Met Met Glu Leu Leu Gly Met Pro Pro Lys Leu
                        420                 425                 430
        Leu Glu Gln Ser Lys Arg Ala Lys Tyr Phe Ile Asn Ser Lys Gly Ile
                    435                 440                 445
        Pro Arg Tyr Cys Ser Val Thr Thr Gln Ala Asp Gly Arg Val Val Leu
                    450                 455                 460
        Val Gly Gly Arg Ser Arg Arg Gly Lys Lys Arg Gly Pro Pro Gly Ser
        465                 470                 475                 480
        Lys Asp Trp Gly Thr Ala Leu Lys Gly Cys Asp Asp Tyr Leu Phe Ile
                        485                 490                 495
        Glu Phe Leu Lys Arg Cys Leu His Trp Asp Pro Ser Ala Arg Leu Thr
                        500                 505                 510
        Pro Ala Gln Ala Leu Arg His Pro Trp Ile Ser Lys Ser Val Pro Arg
                    515                 520                 525
        Pro Leu Thr Thr Ile Asp Lys Val Ser Gly Lys Arg Val Val Asn Pro
                    530                 535                 540
        Ala Ser Ala Phe Gln Gly Leu Gly Ser Lys Leu Pro Pro Val Val Gly
        545                 550                 555                 560
        Ile Ala Asn Lys Leu Lys Ala Asn Leu Met Ser Glu Thr Asn Gly Ser
                        565                 570                 575
        Ile Pro Leu Cys Ser Val Leu Pro Lys Leu Ile Ser
                        580                 585

<210> SEQ ID NO 3
<211> LENGTH: 2327
<212> TYPE: DNA
<213> ORGANISM: Human
```

-continued

<400> SEQUENCE: 3

```
cggcgctggc aagcgaagct tgggggtggg gaggtagagt gagccctcag taggagggac      60
gagggcaggg gtctgactgc ctccccggga ccgccccac ctcctctcta tcagggcccc     120
ctcccccat ccctgtctca ccgggcgcgg gggacggggc tagagcggag ttagagcaag     180
aagaatttcc accccctggat tccctctgaa acccctagatc ggggtatatg ttaagggatt     240
acgaaaatct aggactttt gtggggcttt ttattaaagg gggggagccc gggagcaata     300
ccttggaaag aagccctgtt gcttagagcg ataaccaac ggctgaactc ttggggtttg     360
ctgtgagggg tgcggtctag cttcgaatgt acagtggtgg agccacagtg ttaaagaaca     420
gagaagtgat ccttaatcat ttagaatttt gcctccacca tccaccagaa aatgaagtgg     480
aaagagaagt tgggggatgg tgtctatgac accttcatga tgatagatga aaccaaatgt     540
cccccctgtt caaatgtact ctgcaatcct tctgaaccac ctccacccag aagactaaat     600
atgaccactg agcagtttac aggagatcat actcagcact ttttggatgg aggtgagatg     660
aaggtagaac agctgtttca agaatttggc aacagaaaat ccaatactat tcagtcagat     720
ggcatcagtg actctgaaaa atgctctcct actgtttctc agggtaaaag ttcagattgc     780
ttgaatacag taaaatccaa cagttcatcc aaggcaccca aagtggtgcc tctgactcca     840
gaacaagccc tgaagcaata taaacaccac ctcactgcct atgagaaact ggaaataatt     900
aattatccag aaatttactt tgtaggtcca aatgccaaga aaagacatgg agttattggt     960
ggtcccaata atggagggta tgatgatgca gatggggcct atattcatgt acctcgagac    1020
catctagctt atcgatatga ggtgctgaaa attattggca aggggagttt tgggcaggtg    1080
gccagggtct atgatcacaa acttcgacag tacgtggccc taaaaatggt gcgcaatgag    1140
aagcgctttc atcgtcaagc agctgaggag atccggattt tggagcatct taagaaacag    1200
gataaaactg gtagtatgaa cgttatccac atgctggaaa gtttcacatt ccggaaccat    1260
gtttgcatgg cctttgaatt gctgagcata gacctttatg agctgattaa aaaaaataag    1320
tttcagggtt ttagcgtcca gttggtacgc aagtttgccc agtccatctt gcaatctttg    1380
gatgccctcc acaaaaataa gattattcac tgcgatctga agccagaaaa cattctcctg    1440
aaacaccacg ggcgcagttc aaccaaggtc attgactttg ggtccagctg tttcgagtac    1500
cagaagctct acacatatat ccagtctcgg ttctacagag ctccagaaat catcttagga    1560
agccgctaca gcacaccaat tgacatatgg agttttggct gcatccttgc agaactttta    1620
acaggacagc ctctcttccc tggagaggat gaaggagacc agttggcctc catgatggag    1680
cttctaggga tgccaccacc aaaacttctg gagcaatcca acgtgccaa gtactttatt    1740
aattccaagg gcatacccg ctactgctct gtgactaccc aggcagatgg gagggttgtg    1800
cttgtgggg gtcgctcacg tagggtaaa agcggggtc ccccaggcag caaagactgg    1860
gggacagcac tgaaagggtg tgatgactac ttgtttatag agttcttgaa aaggtgtctt    1920
cactgggacc cctctgcccg cttgaccca gctcaagcat taagacaccc ttggattagc    1980
aagtctgtcc ccagacctct caccaccata gacaaggtgt cagggaaacg ggtagttaat    2040
cctgcaagtg ctttccaggg attgggttct aagctgcctc cagttgttgg aatagccaat    2100
aagcttaaag ctaacttaat gtcagaaacc aatggtagta taccccctatg cagtgtattg    2160
ccaaaactga ttagctagtg gacagagata tgcccagaga tgcatatgtg tatatttta    2220
tgatcttaca aacctgcaaa tggaaaaaat gcaagcccat tggtggatgt ttttgttaga    2280
```

-continued gtagactttt tttaaacaag acaaaacatt tttatatgat tataaaa                    2327

<210> SEQ ID NO 4
<211> LENGTH: 568
<212> TYPE: PRT
<213> ORGANISM: Human

<400> SEQUENCE: 4

Met Lys Trp Lys Glu Lys Leu Gly Asp Gly Val Tyr Asp Thr Phe Met
 1               5                  10                  15

Met Ile Asp Glu Thr Lys Cys Pro Pro Cys Ser Asn Val Leu Cys Asn
            20                  25                  30

Pro Ser Glu Pro Pro Pro Arg Arg Leu Asn Met Thr Thr Glu Gln
        35                  40                  45

Phe Thr Gly Asp His Thr Gln His Phe Leu Asp Gly Gly Glu Met Lys
    50                  55                  60

Val Glu Gln Leu Phe Gln Glu Phe Gly Asn Arg Lys Ser Asn Thr Ile
65                  70                  75                  80

Gln Ser Asp Gly Ile Ser Asp Ser Glu Lys Cys Ser Pro Thr Val Ser
                85                  90                  95

Gln Gly Lys Ser Ser Asp Cys Leu Asn Thr Val Lys Ser Asn Ser Ser
            100                 105                 110

Ser Lys Ala Pro Lys Val Val Pro Leu Thr Pro Glu Gln Ala Leu Lys
        115                 120                 125

Gln Tyr Lys His His Leu Thr Ala Tyr Glu Lys Leu Glu Ile Ile Asn
    130                 135                 140

Tyr Pro Glu Ile Tyr Phe Val Gly Pro Asn Ala Lys Lys Arg His Gly
145                 150                 155                 160

Val Ile Gly Gly Pro Asn Asn Gly Gly Tyr Asp Asp Ala Asp Gly Ala
                165                 170                 175

Tyr Ile His Val Pro Arg Asp His Leu Ala Tyr Arg Tyr Glu Val Leu
            180                 185                 190

Lys Ile Ile Gly Lys Gly Ser Phe Gly Gln Val Ala Arg Val Tyr Asp
        195                 200                 205

His Lys Leu Arg Gln Tyr Val Ala Leu Lys Met Val Arg Asn Glu Lys
    210                 215                 220

Arg Phe His Arg Gln Ala Ala Glu Glu Ile Arg Ile Leu Glu His Leu
225                 230                 235                 240

Lys Lys Gln Asp Lys Thr Gly Ser Met Asn Val Ile His Met Leu Glu
                245                 250                 255

Ser Phe Thr Phe Arg Asn His Val Cys Met Ala Phe Glu Leu Leu Ser
            260                 265                 270

Ile Asp Leu Tyr Glu Leu Ile Lys Lys Asn Lys Phe Gln Gly Phe Ser
        275                 280                 285

Val Gln Leu Val Arg Lys Phe Ala Gln Ser Ile Leu Gln Ser Leu Asp
    290                 295                 300

Ala Leu His Lys Asn Lys Ile Ile His Cys Asp Leu Lys Pro Glu Asn
305                 310                 315                 320

Ile Leu Leu Lys His His Gly Arg Ser Ser Thr Lys Val Ile Asp Phe
                325                 330                 335

Gly Ser Ser Cys Phe Glu Tyr Gln Lys Leu Tyr Thr Tyr Ile Gln Ser
            340                 345                 350

Arg Phe Tyr Arg Ala Pro Glu Ile Ile Leu Gly Ser Arg Tyr Ser Thr
        355                 360                 365

-continued

```
Pro Ile Asp Ile Trp Ser Phe Gly Cys Ile Leu Ala Glu Leu Leu Thr
    370                 375                 380

Gly Gln Pro Leu Phe Pro Gly Glu Asp Glu Gly Asp Gln Leu Ala Ser
385                 390                 395                 400

Met Met Glu Leu Leu Gly Met Pro Pro Lys Leu Leu Glu Gln Ser
                405                 410                 415

Lys Arg Ala Lys Tyr Phe Ile Asn Ser Lys Gly Ile Pro Arg Tyr Cys
            420                 425                 430

Ser Val Thr Thr Gln Ala Asp Gly Arg Val Val Leu Val Gly Gly Arg
            435                 440                 445

Ser Arg Arg Gly Lys Lys Arg Gly Pro Pro Gly Ser Lys Asp Trp Gly
    450                 455                 460

Thr Ala Leu Lys Gly Cys Asp Asp Tyr Leu Phe Ile Glu Phe Leu Lys
465                 470                 475                 480

Arg Cys Leu His Trp Asp Pro Ser Ala Arg Leu Thr Pro Ala Gln Ala
                485                 490                 495

Leu Arg His Pro Trp Ile Ser Lys Ser Val Pro Arg Pro Leu Thr Thr
            500                 505                 510

Ile Asp Lys Val Ser Gly Lys Arg Val Val Asn Pro Ala Ser Ala Phe
        515                 520                 525

Gln Gly Leu Gly Ser Lys Leu Pro Pro Val Val Gly Ile Ala Asn Lys
    530                 535                 540

Leu Lys Ala Asn Leu Met Ser Glu Thr Asn Gly Ser Ile Pro Leu Cys
545                 550                 555                 560

Ser Val Leu Pro Lys Leu Ile Ser
                565
```